United States Patent [19]

Wheeler

[11] Patent Number: 5,176,152

[45] Date of Patent: Jan. 5, 1993

[54] METHOD OF PROVIDING CONVOLUTABLE AREAS ON THERMOPLASTIC ELASTOMERIC FILMS, AND FILMS AND FILM PRODUCTS HAVING SUCH AREAS

[75] Inventor: Robert G. Wheeler, Greenbank, Wash.

[73] Assignee: Family Health International, Durham, N.C.

[21] Appl. No.: 607,292

[22] Filed: Oct. 31, 1990

[51] Int. Cl.⁵ .............................................. A61F 6/04
[52] U.S. Cl. ..................... 128/844; 128/918
[58] Field of Search ............ 128/89 R, 90, 91 R, 128/285, 842, 844, 79, 918; 604/330, 347–353; 264/296; D24/99

[56] References Cited

U.S. PATENT DOCUMENTS

| | | | |
|---|---|---|---|
| D. 253,009 | 9/1979 | Okamoto | D24/99 |
| 2,448,938 | 9/1948 | Wayne | 128/285 |
| 2,586,674 | 2/1952 | Lonne | 128/294 |
| 3,608,268 | 6/1968 | Lauritzen | 53/29 |
| 4,432,357 | 2/1984 | Pomeranz | 128/79 |
| 4,475,910 | 10/1984 | Conway | 604/352 |
| 4,576,156 | 3/1986 | Dyck | 128/132 R |
| 4,684,490 | 8/1987 | Taller | 264/296 |
| 4,685,453 | 8/1987 | Guignard | 128/90 |
| 4,735,621 | 4/1988 | Hessel | 604/349 |
| 4,798,600 | 1/1989 | Meadows | 604/347 |
| 4,817,593 | 4/1989 | Taller | 128/844 |
| 4,955,392 | 9/1990 | Sorkin | 128/844 |

FOREIGN PATENT DOCUMENTS

014707 7/1985 European Pat. Off. .

Primary Examiner—Michael A. Brown
Attorney, Agent, or Firm—Olive & Olive

[57] ABSTRACT

A method of providing a convoluted area on a first thermoplastic elastomeric film, by applying to the film, one or more discrete pieces of a second thermoplastic elastomeric film, wherein the second film is differentially expandable as compared to the underlying first film. The differential expansion may be caused by application of an agent which causes the second film to swell. Products made according to this method may have elongated strips or other shapes of the second film bonded to the first film in areas of the product for which convolutions, puckers or other regular or irregular deformations are desired.

12 Claims, 3 Drawing Sheets

METHOD OF PROVIDING CONVOLUTABLE AREAS ON THERMOPLASTIC ELASTOMERIC FILMS, AND FILMS AND FILM PRODUCTS HAVING SUCH AREAS

BACKGROUND OF THE INVENTION

1. Field of the Invention

This invention pertains to devices made of thermoplastic elastomeric films such as condoms, and in particular, relates to a method for providing convolutions on said films, and to condoms and other devices made of films having portions containing convolutions.

2. Description of the Related Art

Recent significant increases in the incidence and spread of sexually transmitted diseases (STD's), as well as the desire for methods of family planning not requiring use of birth control pills, have resulted in increased use of condoms to reduce transmission both of STD bacteria and of viable sperm.

Condoms are generally elongated tubular sheaths made of a thin flexible material, such as latex resins (natural rubber). Generally, latex resins are used to coat cylindrical molds with a thin layer by a dipping process. The thickness of the rubber coating may vary depending on the viscosity of the latex and the speed of extracting the mold from the latex.

Although, obtaining uniformity is a problem with making condoms of latex, one advantage of natural rubber condoms is that lower initial force is required to stretch a film of natural rubber than to stretch films of many synthetic elastomeric films.

Condoms of a variety of synthetic materials have been developed to improve the strength and reliability characteristics of condoms. It is desirable to use thermoplastic elastomeric films instead of latex or less elastic thermoplastic films because of unique permeability, formability, environmental resistance, mechanical and economy considerations. For example, condoms may be formed of thermoplastic polyurethane materials, such as polyether-or polyester-based urethane elastomers (U.S. Pat. No. 4,576,156 of Dyke), and a polyurethane prepolymer which is the reaction product of a polyisocyanate compound with at least one long chain polyol (Eur. patent application 0 147 072 of Taller et al.). The disclosure of these patents is incorporated herein by reference.

Condoms amenable to construction from thermoplastic elastomeric materials are disclosed in co-pending application, Ser. No. 07/271,884 filed Nov. 15, 1988, the disclosure of which application is hereby incorporated herein.

Specific examples of non-rubber materials used for condoms include, polyurethane materials, for example, the polyesterbased and polyether-based polyurethane materials commercially available from Mobay Corporation such as TEXIN ™,(Plastics and Rubber Division, Pittsburgh, Pa.); the thermoplastic polyurethane elastomers which are commercially available from BASF Corporation (Parsippany, N.J.) under the trademark ELASTOLLAN ™ (PLATILON ™); polyester elastomers, such as the block copolymers of polybutylene terephthalate and long chain polyether glycols, which are commercially available from E. I. DuPont de Nemours and Co., Inc. (Polymer Products Dept., Engineering Polymers Div., Wilmington, Del.) under the trademark HYTREL ™; other polyester polyurethane elastomers such as PELLETHANE ™ (Bertek, St. Albans, Vt.); polyether blockamides, such as those commercially available from Atochem, Inc. (Glenrock, N.J.) under the trademark PEBAX ™; multiblock rubberbased copolymers, such as are commercially available from Shell Chemical Co. (Houston, Tex.) under the trademark KRATON ™; ethylene-octene copolymers such as those commercially available from the Dow Chemical Co. (Midland, Mich.) under the trademark ATTANE ™, as well as any other suitable homopolymers and copolymers, and mixtures, alloys, and composites thereof.

The synthetic materials used for condoms generally have less elasticity (more resistance to stretch) and show more viscoelastic creep than natural rubber. The higher elastic modulus of thermoplastic elastomers causes them to be less desirable for condoms than latex because of a greater stiffness. The lower creep resistance of thermoplastic elastomers causes a problem because they lose their shape when they are rolled for packaging.

The elastic moduli of many thermoplastic elastomers that might be or are being used for condoms are high relative to latex and do not allow for easy donning of the condoms and a secure fit over a wide range of penis circumferences.

Resin suppliers and manufacturers have attempted to remedy this situation by altering the chemical composition of the synthetic polymers and by adding plasticizers. Softening with plasticizer complicates the governmental approval process for intimate human use and causes undesirable changes in some mechanical properties such as tear resistance.

Thermoplastic films as produced by casting, extrusion or by extrusion blowing are generally in the form of flat planar films rolled onto reels. Many of the applications of the films in the form of bags, covers, garments, pouches and the like require that the film be wrinkled or folded to make it conform to a surface that cannot be generated from a planar film. An alternative is to take a planar film that has been highly folded throughout and to make it conform to irregular shapes by stretching. When the pattern of convolutions in the film has a curvature to film thickness ratio that allows the film to be flattened without exceeding its elastic limit, it will behave as an elastic membrane when it is stretched and contracted reversibly.

A patent application is in preparation entitled "TEXTURED THERMOPLASTIC ELASTOMERIC FILM AND ARTICLES COMPRISING SAME," which discloses a method of improving film elasticity of thermoplastic elastomeric films by heat embossing (texturizing) the film, and items made from such film. This texture is a "microtexture" and provides a limited stretching range before the embossing is exhausted and causes thinning of the film.

One way of obtaining differential effects on various portions of metallic materials after exposure to certain treatment parameters utilizes bimetallic strips. Such strips increase in curvature with temperature because the two components have different thermal coefficients of expansion. Such differential expansion is useful to provide a controlled change in form of a metallic substance at a given treatment time.

It is therefore an object of the invention to provide films having areas of different coefficients of solvent-mediated expansion, for example, of hydroscopic expansion.

It is also an object of this invention to provide a method for treating elastomeric film so that large changes may be produced in the area covered by the film without changing the film thickness or surface area of the film.

It is a further object of the invention to provide a means for treating a portion of an elastomeric film so that portion is self-puckering into convolutions when treated with an appropriate agent.

It is a further object of the invention to provide items made from elastomeric film, and which have all or a portion of the item treated to self-pucker and/or form convolutions when treated with an agent.

It is a further object of the invention to provide items which have a plurality of self-puckering areas.

It is a further object of the invention to provide thermoplastic films capable of conforming reversibly to irregular shapes.

Other objects and advantages of the invention will be more fully apparent from the following disclosure and appended claims.

SUMMARY OF THE INVENTION

The invention pertains to a process for converting planar thermoplastic film into a highly convoluted surface which may have uniform convolutions and in which the original planar configuration can be restored by stretching the film. The invention further pertains to items made of a first thermoplastic film which film has one or more areas made so that treatment with an agent results in puckering of these areas to a highly convoluted surface. In areas where puckering is desired, pieces which preferably are elongated strips of a second thermoplastic elastomeric film that is differentially swellable with respect to the first film are bonded so that each strip is spaced apart from the adjacent strip or strips.

Other aspects and features of the invention will be more fully apparent from the following disclosure and appended claims.

DETAILED DESCRIPTION OF THE INVENTION AND PREFERRED EMBODIMENTS THEREOF

Figure 1:
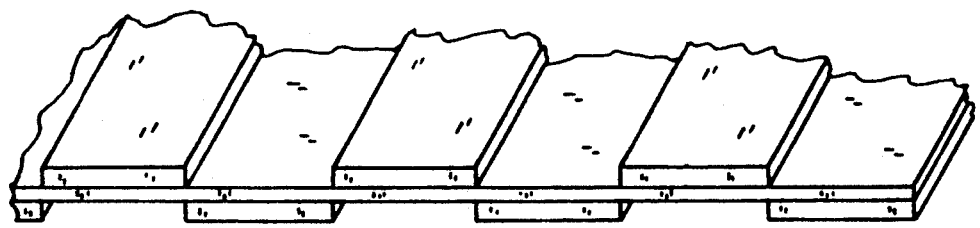
FIG. 1 is a perspective view of an end of a piece of self-puckering film prepared according to the invention prior to treatment with a puckering agent.
Figure 2:
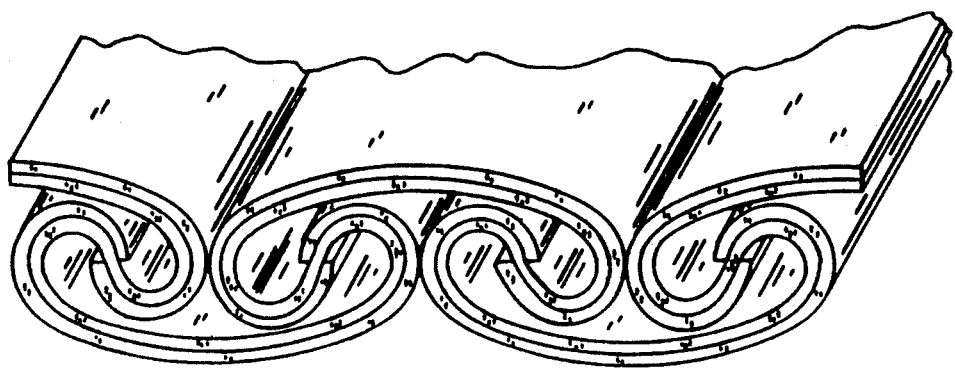
FIG. 2 is a perspective view of an end of a piece of self-puckering film according to FIG. 1 after treatment with a puckering agent.

As shown in FIGS. 1 and 2, the method of the invention for forming a convolutable or self-puckering area on a thermoplastic elastomeric film comprises the steps of:

(a) providing a first thermoplastic elastomeric film 20;
(b) providing pieces 22 of a second thermoplastic elastomeric film, said first and second thermoplastic elastomeric films being differentially swellable by use of an agent; and
(c) bonding the pieces 22 to the first thermoplastic elastomeric film 20.

Preferably, the pieces 22 of the second film are elongated strips. The strips of the second film are preferably bonded in a parallel or approximately parallel array 24 on an area of the first thermoplastic film The method of this invention provides a means of converting planar thermoplastic films into a uniformly highly convoluted surface in which the original planar configuration can be restored by stretching the film. A bellows is an example of a highly folded non-elastic film that when stretched has the original planar configuration restored.

The invention relies on the fact that if one side of a flat film is under tension and the opposing side is under compression, the film will have a tendency to roll itself into a scroll. Hence, if a film that is swellable by a solvent is laminated with a film that is not swollen by the solvent, it will remain flat in the absence of the solvent, and will roll itself into a scroll in the presence of the solvent. Conversely, if a solvent-swollen film is laminated with a film not affected by the solvent, the composite film will be flat in the presence of the solvent and self-scroll when the solvent evaporates.

Although the preferred embodiments of this invention utilize solvent agents, it is contemplated that other agents, such as temperature, other chemical agents, etc. may be used with proper selection of different films to cause puckering through differential film expansion upon exposure to the chosen agent.

As used herein the terms "self-puckering" (or "puckering") or "convolutable" refer to the characteristic of portions of a film of the invention to change from a first relatively planar film form to a second form having different elevations, ripples, convolutions, and/or puckered areas. This change is caused by the differential expansion of the strips as compared to the planar first film as a biaxial load is placed on the underlying first film. If a first film has bonded to it a plurality of parallel or approximately parallel strips of a second film, the second form is a highly convoluted film in which the convolutions extend in a roughly parallel fashion along the length of the bonded strips. Such film is convolutable in the strip-laminated areas but remains planar in the remaining areas remote from the laminated areas. If the first and second films of the same size are laminated and then treated with solvent, the composite becomes a multi-directional scrollable piece, the direction of scroll being determined by the direction of initial impulse. Other shapes and sizes of the second film pieces which are laminated to the first film may clearly be used to obtain particular desired deformations, convolutions and puckerings of the product.

In the preferred embodiment, such a change is due to addition of an agent which differentially causes swelling of the strips or squares but not of the underlying first film. The agent may be water or some other solvent. Alternatively, the already swollen strips may be bonded to a nonswellable first film so that when the film dries it forms convolutions but is planar when treated with or in the presence of the solvent.

The first thermoplastic elastomeric film may be, for example, any polyether or polyester based polyethane as are used in condom fabrication and as are discussed herein. Preferred first elastomeric films include polyurethane (ELASTOLLAN 1185, Atochem, Inc. (Glennrock, N.J.) and TEXIN, (Mobay Corp., Pittsburgh, Pa.)).

The second thermoplastic elastomeric film may be any film that is swellable by a swelling agent. Such swelling is preferably reversible, so that the presence of swelling is controllable. A preferred second film is PEBAX 4011 of Atochem Co., a hydrophyllic film that is swollen by water.

The features and advantages of the present invention will be more clearly understood by reference to the following examples, which are not to be construed as limiting the invention.

EXAMPLE I

Formation of a Convolutable Laminate

Strips 22 of a thermoplastic elastomeric film (PEBAX 4011, Atochem Co.) that is swellable by water are bonded to a sheet 20 of polyurethane film (ELASTOLLAN 1185). The strips may be bonded at spaced intervals to one side of the film only or may be also be placed on the second side of the film as illustrated in FIG. 1. The width of the PEBAX strips 22 may vary from 1 to 10 mm, and is preferably about 4 to 8 mm for small items such as condoms where very large surface variations may not be desirable. Lamination of the films is accomplished in a hot platen press at a pressure on the film of 1000 psi and a temperature of 250° F. When moistened with water the laminated film 14 of FIG. 1 assumes the convoluted form illustrated in FIG. 2.

EXAMPLE II

Formation a Condoms with Multiple Convolutable Areas

Figure 3:
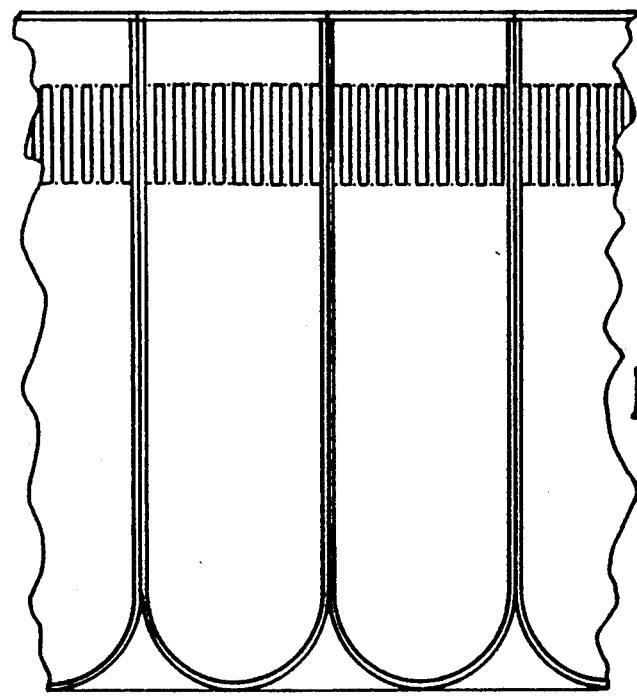
FIG. 3 is a planar view of a strip of polyurethane film to which PEBAX strips are bonded according to the invention.

For condoms made of two elongated pieces of polyurethane film which are heat sealed together along the side and lower edges, there may be PEBAX strips 22 placed between the two pieces on the inside of the area that is to be the rim (22A), on the area that is to be the neck area (22B) and on the outside directly over the gaps between strips 22B (22C) on each of the two sheets and laminated to the sheets. A cross-section of the neck area appears as in FIG. 1. One such sheet is shown in FIG. 3. To form the condom, the two sheets are placed together and heat sealed together along seal line 16 into a straight-sided condom with no rim.

Figure 4:
FIG. 4 is a perspective view of a condom having two selfpuckering areas, prepared with the film of FIG. 3, and treated with an agent.

When the condom is moistened with water (FIG. 4), the top ¾ inch automatically rolls itself into a rim 28 due to strip(s) 22A, and an elastic cuff 30 forms at the top due to strips 22B and 22C to provide a means of retention on the penis. The condom may be placed over a mandrel and rolled into the conventional shape for packaging (not shown). When packaged in a water-based lubricant and a foil protected sachet, the shape resulting from the presence of moisture will be retained indefinitely.

EXAMPLE III

Formation of a Condom which Is Circumferentially Convolutable

Figure 5:
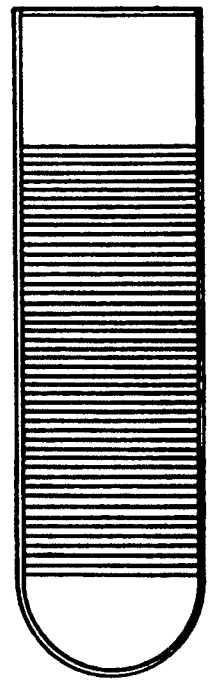
FIG. 5 is a perspective view of a condom having strips extending circumferentially and not treated with an agent.
Figure 6:
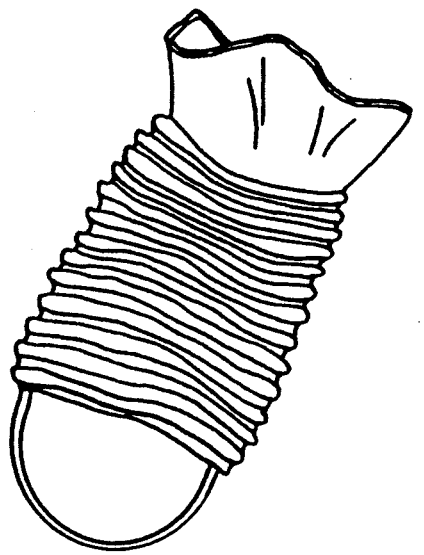
FIG. 6 is a perspective view of the condom of FIG. 5 after treatment with an agent.
Figure 7:
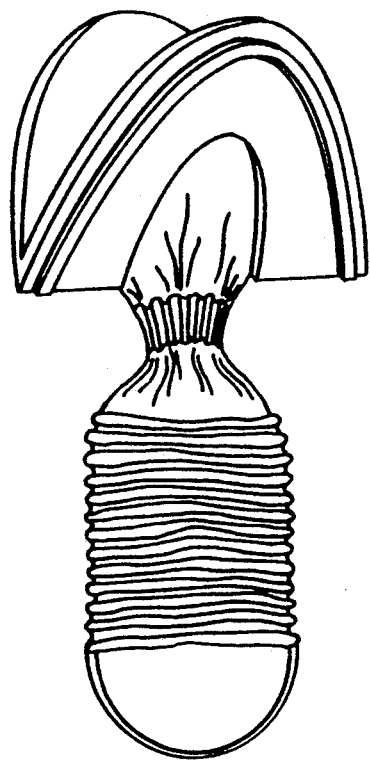
FIG. 7 is a perspective view of a protective vaginal liner having circumferential and axial puckering.
Figure 8:
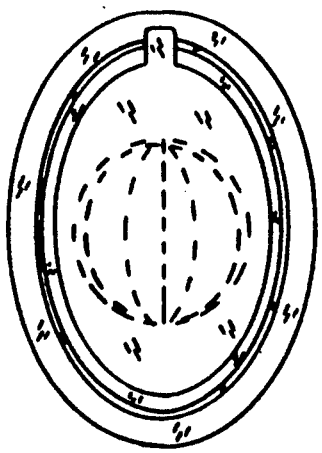
FIG. 8 is a schematic view of the open end of the liner of FIG. 7.

The condom is made of 50 um thick ELASTOLLAN and with 1/10 inch wide PEBAX 4011 strips 22 spaced ¼ inch apart, each strip extending circumferentially around the condom preferably on the outside (FIG. 5), but the strips may be placed on the inside or on both the inside and outside. There is a one inch wide bipolymeric section 32 at the inside of the open end to form a rolled rim when the condom is moistened (FIG. 6). Such a wide strip at the rim is not necessary. A strip of PEBAX 4011 as narrow as one mm wide bonded to a piece of ELASTOLLAN is sufficient to form a narrow rolled ridge on the ELASTOLLAN when the composite is moistened.

EXAMPLE IV

Formation of a Vaginal Liner Having Convolutable Areas

A protective vaginal liner (PVL) 34 may be made which utilizes a bikini-type garment with an opening in the crotch made to accept the ziplock rim 36 on the flange 38 of the PVL. A zip-lock rim on the opening in the crotch of the garment should probably be on the inside to improve its holding to the PVL over that of an outside position. Optionally, the PVL may be used without the bikini.

The starting shape of the PVR is much like the early heatsealed polyurethane condoms having an oval flange at their opening. This shape is modified, however, by heat sealing PEBAX 4011 strips 22 about 0.1 inches wide and spaced 0.25 inches apart to the outside of the PVL. The introitus 40 has the PEBAX strips 22D about one inch long oriented axially. When packaged in a water-base lubricant, these strips 22D cause the opening to pucker and form the introitus section.

The body of the PVL 34 is pliably cylindrical in shape and has the PEBAX strips 22E oriented circumferentially both within and on the outside of the PVL. When moist, these strips cause the body of the PVL to contract from about six inches long to about a three inch length. A small axial force on the end 42 of the PVL will extend the body to its full length.

In an alternative embodiment all the PEBAX strips are bonded to the outside of the PVL so that fabrication is made easier. This results in some loss of contraction properties that could be available if strips on the inside matched the openings between the strips on the outside, but the PVL is still contracts to form a suitable vaginal liner.

To package the disposable portion of the PVL, its body is compressed into a thin ring against the flange 38 and a vapor proof peel-away cover 44 with a tab 46 is placed over both the inside and the outside of the flange. The package cover does not enclose the zip-lock rim 36 so that the PVL may be attached to the bikini with the covers in place.

There are many variations in the way the PVL might be used. Immediately prior or long before anticipated sex, the female may don the bikini with the PVL in place and both the protective covers removed. With her fingers or some other appropriate object, the body of the PVR could be pressed into her vagina or optionally it could remain in its compressed shape. If it is to remain compressed, it would be unnecessary to remove the outside protective cover. Otherwise the cover would be removed temporarily and then replaced to prevent seepage of lubricant. Another option would be to allow the male to use the PVL without the bikini and insert it as an ordinally condom would be inserted. With the bikini, the PVL might be inverted so that the body faces outside and the insertion is completed with the male penis.

While the invention has been described with reference to specific embodiments thereof, it will be appreciated that numerous variations, modifications and embodiments are possible, and accordingly, all such variations, modifications and embodiments are regarded as being within the spirit and scope of this invention.

What is claimed is:

1. A method of forming a convolutable area on a thermoplastic elastomeric film comprising:
   (a) providing a first thermoplastic elastomeric film;
   (b) providing pieces of a second thermoplastic elastomeric film, said first and second thermoplastic elastomeric films being differentially swellable by use of an agent; and
   (c) bonding the strips to the first thermoplastic elastomeric film in the area on the first film being formed into a convolutable area.

2. A method according to claim 1, wherein the pieces are elongated and are bonded parallel to each other on the first thermoplastic elastomeric film.

3. A method according to claims 1, wherein a plurality of convolutable areas are formed on the first thermoplastic elastomeric film.

4. A method according to claim 2, wherein pieces of the second thermoplastic elastomeric film are bonded to both sides of the first film.

5. A method according to claim 1, wherein the pieces of the second film and the first film are bonded together at a pressure of about 1000 psi and a temperature of about 250° F.

6. A method according to claim 1, wherein the first thermoplastic elastomeric film comprises polyurethane film.

7. A method according to claim 1, wherein the first film is not swellable in the presence of the agent and the second thermoplastic elastomeric film comprises a film that is swellable in the presence of the agent.

8. A method according to claim 1, where the second thermoplastic film is hygroscopic and the agent is water.

9. A product made of thermoplastic elastomeric film, having one or more areas in which pieces of a second thermoplastic elastomeric film are bonded to a first thermoplastic elastomeric film, said first and second thermoplastic elastomeric films being differentially swellable by use of an agent, wherein the product is a condom having a tubular body and elongated pieces of the second thermoplastic elastomeric film are bonded circumferentially around said tubular body.

10. A product made of thermoplastic elastomeric film, having one or more areas in which pieces of a second thermoplastic elastomeric film are bonded to a first thermoplastic elastomeric film, said first and second thermoplastic elastomeric films being differentially swellable by use of an agent, wherein elongated pieces of the second thermoplastic elastomeric film are bonded to the condom on the tubular body and extending co-linearly with the tubular body, and wherein near the opening, elongated pieces of the second thermoplastic elastomeric film are bonded circumferentially about the tubular body.

11. A product made of thermoplastic elastomeric film, having one or more areas in which pieces of a second thermoplastic elastomeric film are bonded to a first thermoplastic elastomeric film, said first and second thermoplastic elastomeric films being differentially swellable by use of an agent, wherein the product is a protective vaginal liner having an introitus and a bag-shaped body and elongated pieces of the said thermoplastic elastomeric film are bonded with an axial orientation on the introitus.

12. A product according to claim 11, wherein elongated pieces of the second thermoplastic elastomeric film are also bonded circumferentially about the body.

* * * * *

UNITED STATES PATENT AND TRADEMARK OFFICE
CERTIFICATE OF CORRECTION

PATENT NO. : 5,176,152
DATED : January 5, 1993
INVENTOR(S) : Wheeler, Robert G.

It is certified that error appears in the above-indentified patent and that said Letters Patent is hereby corrected as shown below:

Column 1, line 6, insert the following:

-- GOVERNMENT LICENSE RIGHTS

The invention claimed herein was made under one or more of the following contracts: U.S. Agency for International Development Contract Nos. DPE-3041-A-00-0043 and DPE-0537-A-00-4047, and National Institutes of Heal Contract No. N01-HD-2-3143, and the U.S. Government has certain rights therein. --

Signed and Sealed this

Fifteenth Day of April, 1997

Attest:

BRUCE LEHMAN

Attesting Officer

Commissioner of Patents and Trademarks